United States Patent
Jinqi et al.

(10) Patent No.: US 9,470,613 B2
(45) Date of Patent: Oct. 18, 2016

(54) APPARATUS FOR DETECTING SPRING STIFFNESS

(71) Applicant: CITIC Dicastal Co., Ltd., Qinhuangdao (CN)

(72) Inventors: Lyu Jinqi, Qinhuangdao (CN); Sun Hanbao, Qinhuangdao (CN); Tang Debin, Qinhuangdao (CN); Liu Chunhai, Qinhuangdao (CN); Zhu Zhihua, Qinhuangdao (CN); Wang Yongning, Qinhuangdao (CN); Li Changhai, Qinhuangdao (CN)

(73) Assignee: Citic Dicastal Co. Ltd, Qinghuangdao (CN)

( * ) Notice: Subject to any disclaimer, the term of this patent is extended or adjusted under 35 U.S.C. 154(b) by 0 days.

(21) Appl. No.: 14/656,592

(22) Filed: Mar. 12, 2015

(65) Prior Publication Data
US 2015/0260623 A1    Sep. 17, 2015

(30) Foreign Application Priority Data
Mar. 14, 2014 (CN) .......................... 2014 1 0093930

(51) Int. Cl.
*G01N 3/08* (2006.01)

(52) U.S. Cl.
CPC ......... *G01N 3/08* (2013.01); *G01N 2203/0288* (2013.01)

(58) Field of Classification Search
CPC ........................ G01N 2203/0286; G01N 3/08
See application file for complete search history.

(56) References Cited

U.S. PATENT DOCUMENTS

| | | | | |
|---|---|---|---|---|
| 1,992,987 A * | 3/1935 | Bitzer | ...................... | G01N 3/00 73/161 |
| 2,414,550 A * | 1/1947 | Patch | ....................... | G01N 3/08 73/803 |
| 2,518,408 A * | 8/1950 | Weyand | .................... | G01N 3/00 73/161 |
| 3,566,694 A * | 3/1971 | Vogel et al. | .............. | G01L 7/16 73/1.15 |
| 3,643,496 A * | 2/1972 | Zajic | ......................... | G01N 3/10 73/816 |
| 3,675,479 A * | 7/1972 | Carlson | .................... | G01N 3/00 73/161 |
| 5,119,681 A * | 6/1992 | Miszczak | ............ | G01M 13/005 73/37 |
| 5,211,061 A * | 5/1993 | Goodwin | ................. | B23P 19/06 702/41 |
| 5,669,598 A * | 9/1997 | Ticey | ......................... | F16F 1/32 267/162 |
| 5,832,774 A * | 11/1998 | Smith | ...................... | G01N 3/00 73/161 |
| 6,671,632 B2 * | 12/2003 | Sridhar | .................... | G01N 3/00 702/33 |
| 7,753,339 B2 * | 7/2010 | Yuzawa | .................. | F16K 41/02 251/214 |
| 8,366,082 B2 * | 2/2013 | Evans | ....................... | F16F 1/32 267/162 |

\* cited by examiner

*Primary Examiner* — Lisa Caputo
*Assistant Examiner* — Tran M Tran
(74) *Attorney, Agent, or Firm* — Platinum Intellectual Property LLP

(57) ABSTRACT

The present invention discloses an apparatus for detecting spring stiffness which comprises a universal material testing machine, a loading beam of the universal material testing machine, a fixing rod of bracket for Belleville spring deformation detection, a movable clamping rod of bracket for Belleville spring deformation detection, a dial gauge, etc.

1 Claim, 1 Drawing Sheet

APPARATUS FOR DETECTING SPRING STIFFNESS

TECHNICAL FIELD

The present invention relates to a stiffness detecting apparatus.

BACKGROUND OF THE INVENTION

Belleville spring has a conical disk shape, which plays unique functions different from conventional springs. Major characteristics of Belleville spring include higher load carrying capacity, shorter stroke, smaller space required, convenience in combined using, easy repair and replacement as well as higher security and lower cost. Accordingly, Belleville spring is suitable for being used in sophisticated heavy machinery occupying smaller space and bearing higher load. The optimal working range of the Belleville spring is from 10% to 75% of its maximum compression stroke.

The design, purchase and replacement of the Belleville spring are dependent upon its stiffness. Therefore, it is significant to detect the stiffness of the Belleville spring.

SUMMARY OF THE INVENTION

It is an object of the present invention to provide an apparatus for detecting stiffness of Belleville spring.

The apparatus for detecting stiffness of Belleville spring comprises: a universal material testing machine, a loading beam of the universal material testing machine, a first fixing rod of bracket for Belleville spring deformation detection, a first movable clamping rod of bracket for Belleville spring deformation detection, a first dial gauge, a loading linkage, a spherical squeezing head, a second dial gauge, a cup-shaped loading barrel, a Belleville spring, a guide base, a second movable clamping rod of bracket for Belleville spring deformation detection, and a second fixing rod of bracket for Belleville spring deformation detection.

The guide base is placed on the table portion of the universal material testing machine, with the axis of the guide base coincident with that of the loading beam of the universal material testing machine. The guide base is a shaft with stepped structure and smooth surface.

The Belleville spring is placed on the guide base. By adjusting the relative position of the Belleville spring in relation to the guide base, the axis of the Belleville spring is made coincident with that of the guide base.

The cup-shaped loading barrel is placed on the Belleville spring. As a cylinder with stepped structure, the cup-shaped loading barrel is provided with a spherical recess at the center of its bottom surface, which mates with the spherical squeezing head to eliminate biased loading.

One end of the loading linkage is coupled to the loading beam of the universal material testing machine by means of thread connection, and the other end is coupled to the spherical squeezing head also by means of thread connection.

The first fixing rod of bracket for Belleville spring deformation detection and the second fixing rod of bracket for Belleville spring deformation detection are symmetrically fixed on the table portion of the universal material testing machine respectively at two sides of the guide base.

The first movable clamping rod of bracket for Belleville spring deformation detection is mounted on the first fixing rod of bracket for Belleville spring deformation detection. The first dial gauge is then clamped on the first movable clamping rod of bracket for Belleville spring deformation detection. By adjusting the first fixing rod of bracket for Belleville spring deformation detection, the first movable clamping rod of bracket for Belleville spring deformation detection and the first dial gauge, the first dial gauge is put into good contact with the outer surface of the bottom of the cup-shaped loading barrel and is kept with a pre-compression of 1-2 mm.

The second movable clamping rod of bracket for Belleville spring deformation detection is mounted on the second fixing rod of bracket for Belleville spring deformation detection. Then, the second dial gauge is clamped on the second movable clamping rod of bracket for Belleville spring deformation detection. By adjusting the second movable clamping rod of bracket for Belleville spring deformation detection, the second fixing rod of bracket for Belleville spring deformation detection and the second dial gauge, the second dial gauge is put into good contact with the outer surface of the bottom of the cup-shaped loading barrel and is kept with a pre-compression of 1-2 mm.

Load is applied by means of the loading beam of the universal material testing machine, which is then transmitted onto the cup-shaped loading barrel via the loading linkage and the spherical squeezing head, then evenly onto the Belleville spring via the cup-shaped loading barrel. The deformation amount of the Belleville spring is obtained by readings of the first dial gauge and the second dial gauge. At the same time, the value of force exerted by the universal material testing machine is recorded. The stiffness value of the Belleville spring could be calculated by introducing the deformation amount value and the force value into calculation formulas.

The present invention employs the universal material testing machine as a force loading source, and load is exerted onto the Belleville spring through the spherical loading device. Two symmetrically placed dial gauges are used to detect the deformation amount of the Belleville spring in order to check on whether biased loading is provided by the loading device. If the readings of said two symmetrically placed dial gauges are different, there must be biased force loading. Under this circumstance, it is imperative to adjust such force transmission devices as the Belleville spring and the guide barrel, until the biased loading is eliminated.

DETAILED DESCRIPTION OF THE EMBODIMENTS

Figure 1:
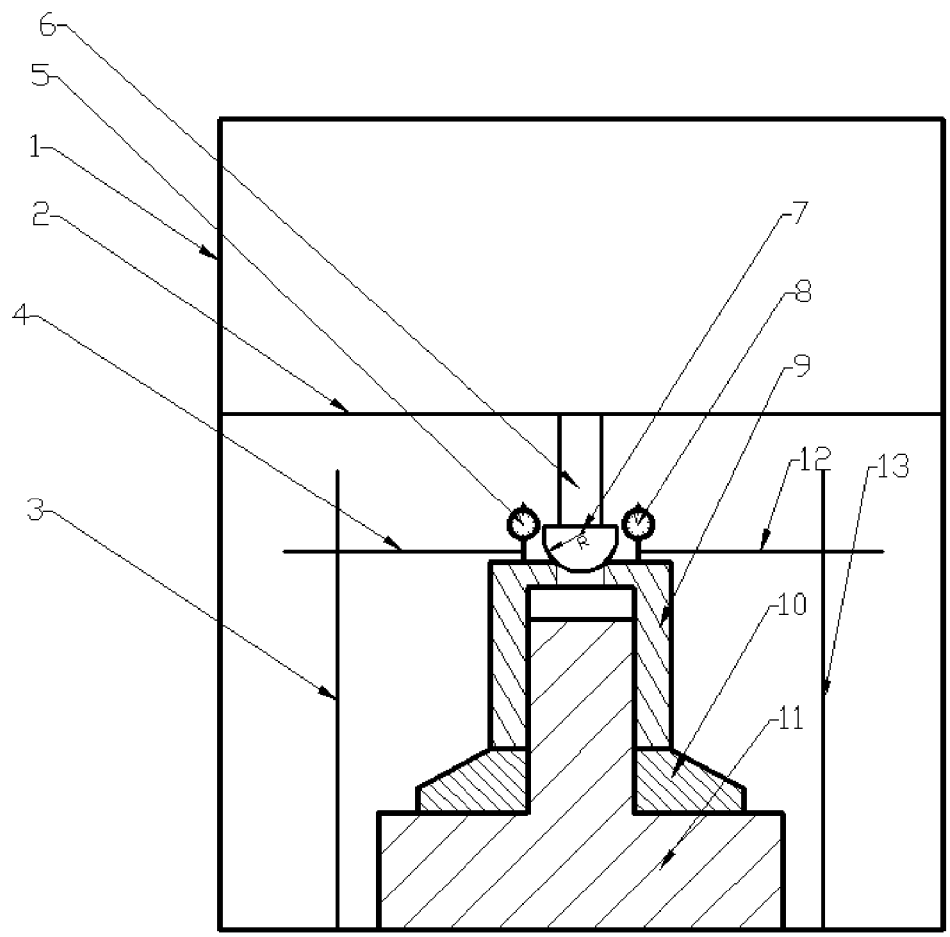
FIG. 1 is a structural schematic view of an apparatus for detecting spring stiffness of the present invention.
Figure 2:
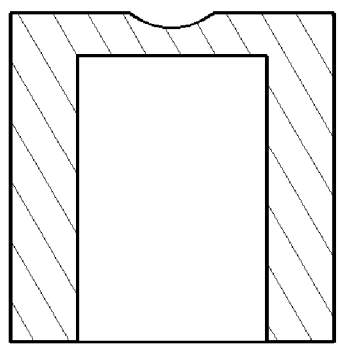
FIG. 2 is a structural schematic view of the cup-shaped loading barrel of the apparatus for detecting spring stiffness of the present invention.

The apparatus for detecting Belleville spring stiffness will be described in detail in conjunction with the drawings.

The apparatus for detecting Belleville spring stiffness comprises: a universal material testing machine 1, a loading beam 2 of the universal material testing machine, a first fixing rod of bracket for Belleville spring deformation detection 3, a first movable clamping rod of bracket for Belleville spring deformation detection 4, a first dial gauge 5, a loading linkage 6, a spherical squeezing head 7, a second dial gauge 8, a cup-shaped loading barrel 9, a Belleville spring 10, a guide base 11, a second movable clamping rod of bracket for Belleville spring deformation detection 12, and a second fixing rod of bracket for Belleville spring deformation detection 13.

The guide base 11 is placed on the table portion of the universal material testing machine 1, with the axis of the guide base 11 coincident with that of the loading beam 2 of the universal material testing machine. The guide base 11 is a shaft with stepped structure and smooth surface.

Belleville spring 10 is placed on the guide base 11. By adjusting the relative position of the Belleville spring 10 in relation to the guide base 11, the axis of the Belleville spring 10 is made coincident with that of the guide base 11.

The cup-shaped loading barrel 9 is placed on the Belleville spring 10. As a cylinder with stepped structure, the cup-shaped loading barrel 9 is provided with a spherical recess at the center of its bottom surface, which mates with the spherical squeezing head 7 to eliminate biased loading.

One end of the loading linkage 6 is coupled to the loading beam 2 of the universal material testing machine by means of thread connection, and the other end is coupled to the spherical squeezing head 7 also by means of thread connection.

The first fixing rod of bracket for Belleville spring deformation detection 3 and the second fixing rod of bracket for Belleville spring deformation detection 13 are symmetrically fixed on the table portion of the universal material testing machine at two sides of the guide base 11.

The first movable clamping rod of bracket for Belleville spring deformation detection 4 is mounted on the first fixing rod of bracket for Belleville spring deformation detection 3. The first dial gauge 5 is then clamped on the first movable clamping rod of bracket for Belleville spring deformation detection 4. By adjusting the first fixing rod of bracket for Belleville spring deformation detection 3, the first movable clamping rod of bracket for Belleville spring deformation detection 4 and the first dial gauge 5, the first dial gauge 5 is put into good contact with the outer surface of the bottom of the cup-shaped loading barrel 9 and is kept with a pre-compression of 1-2 mm.

The second movable clamping rod of bracket for Belleville spring deformation detection 12 is mounted on the second fixing rod of bracket for Belleville spring deformation detection 13. Then, the second dial gauge 8 is clamped on the second movable clamping rod of bracket for Belleville spring deformation detection 12. By adjusting the second movable clamping rod of bracket for Belleville spring deformation detection 12, the second fixing rod of bracket for Belleville spring deformation detection 13 and the second dial gauge 8, the second dial gauge 8 is put into good contact with the outer surface of the bottom of the cup-shaped loading barrel 9 and is kept with a pre-compression of 1-2 mm.

Load is applied by means of the loading beam 2 of the universal material testing machine 1, which is then transmitted onto the cup-shaped loading barrel 9 via the loading linkage 6 and the spherical squeezing head 7, then evenly onto the Belleville spring 10 via the cup-shaped loading barrel 9. The deformation amount of the Belleville spring 10 is obtained by readings of the first dial gauge 5 and the second dial gauge 8. At the same time, the value of force exerted by the universal material testing machine 1 is recorded. The stiffness value of the Belleville spring could be calculated by introducing the deformation amount value and the force value into calculation formulas.

The invention claimed is:

1. An apparatus for detecting spring stiffness comprising a universal material testing machine (1), a loading beam of the universal material testing machine (2), a first fixing rod of bracket for Belleville spring deformation detection (3), a first movable clamping rod of bracket for Belleville spring deformation detection (4), a first dial gauge (5), a force loading linkage (6), a spherical squeezing head (7), a second dial gauge (8), a cup-shaped loading barrel (9), a Belleville spring (10), a guide base (11), a second movable clamping rod of bracket for Belleville spring deformation detection (12), and a second fixing rod of bracket for Belleville spring deformation detection (13), wherein the guide base (11) is configured to be placed on a table portion of the universal material testing machine (1), with an axis of the guide base (11) coincident with that of the loading beam (2) of the universal material testing machine; the guide base (11) is a shaft with stepped structure and smooth surface; the Belleville spring (10) is configured to be placed on the guide base (11), with an axis of the Belleville spring (10) coincident with that of the guide base (11);

wherein the cup-shaped loading barrel (9) is configured to be placed on the Belleville spring (10) and is provided with a spherical recess at the center of its bottom surface, which mates with the spherical squeezing head (7);

wherein one end of the force loading linkage (6) is configured to be coupled to the loading beam (2) of the universal material testing machine by means of thread connection, and the other end is configured to be coupled to the spherical squeezing head (7) also by means of thread connection;

wherein the first fixing rod of bracket for Belleville spring deformation detection (3) and the second fixing rod of bracket for Belleville spring deformation detection (13) are configured to be symmetrically fixed on the table portion of the universal material testing machine (1) at two sides of the guide base (11);

wherein the first movable clamping rod of bracket for Belleville spring deformation detection (4) is configured to be mounted on the first fixing rod of bracket for Belleville spring deformation detection (3), the first dial gauge (5) is configured to be clamped on the first movable clamping rod of bracket for Belleville spring deformation detection (4); the second movable clamping rod of bracket for Belleville spring deformation detection (12) is configured to be mounted on the second fixing rod of bracket for Belleville spring deformation detection (13), the second dial gauge (8) is configured to be clamped on the second movable clamping rod of bracket for Belleville spring deformation detection (12); and wherein load is provided by means of the loading beam (2) of the universal material testing machine (1), which is then transmitted onto the cup-shaped loading barrel (9) via the loading linkage (6) and the spherical squeezing head (7), then evenly onto the Belleville spring (10) via the cup-shaped loading barrel (9), and the deformation amount of the Belleville spring (10) is obtained by readings of the first dial gauge (5) and the second dial gauge (8).

* * * * *